US010786650B2

(12) United States Patent
Burkholz et al.

(10) Patent No.: US 10,786,650 B2
(45) Date of Patent: Sep. 29, 2020

(54) CATHETER ADAPTER PROVIDING CATHETER KINK RESISTANCE (71) Applicant: Becton, Dickinson and Company, Franklin Lakes, NJ (US)

(72) Inventors: Jonathan Karl Burkholz, Salt Lake City, UT (US); Troy Atkin, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 643 days.

(21) Appl. No.: 15/285,585

(22) Filed: Oct. 5, 2016

(65) Prior Publication Data
US 2017/0119997 A1 May 4, 2017

Related U.S. Application Data (60) Provisional application No. 62/247,256, filed on Oct. 28, 2015.

(51) Int. Cl.
*A61M 25/00* (2006.01)
*A61M 25/06* (2006.01)
*A61M 39/10* (2006.01)

(52) U.S. Cl.
CPC ...... *A61M 25/008* (2013.01); *A61M 25/0014* (2013.01); *A61M 25/0043* (2013.01);
(Continued)

(58) Field of Classification Search
CPC ............ A61M 25/008; A61M 25/0014; A61M 25/0043; A61M 25/0097; A61M 25/0606
(Continued)

(56) References Cited

U.S. PATENT DOCUMENTS 3,915,168 A 10/1975 Monestere, Jr. et al.
4,874,378 A 10/1989 Hillstead
(Continued)

FOREIGN PATENT DOCUMENTS

CN 1520322 A 8/2004
CN 101925378 A 12/2010
(Continued)

OTHER PUBLICATIONS

PCT International Preliminary Report on Patentability in PCT/US2016/055666 dated May 11, 2018, 8 pages.
(Continued)

*Primary Examiner* — Phillip A Gray
(74) *Attorney, Agent, or Firm* — Servilla Whitney LLC (57) ABSTRACT

A vascular access device is disclosed including a catheter, a catheter adapter having a distal end and a proximal end, an overall length extending from the distal end to the proximal end, an internal cavity, an upper portion, a lower portion and a tip having a distal opening having a circumference through which the catheter extends, an introducer needle extending through the catheter; and a needle hub connected to the proximal end of the introducer needle. The catheter adapter being connected to the proximal end of the catheter and at least a majority of the catheter adapter is made from a first material and at least a portion of the tip is made from a second material that is more flexible than the first material.

28 Claims, 10 Drawing Sheets

(52) U.S. Cl.
CPC .... *A61M 25/0097* (2013.01); *A61M 25/0606* (2013.01); *A61M 25/0637* (2013.01); *A61M 39/10* (2013.01); *A61M 2025/0059* (2013.01); *A61M 2025/0098* (2013.01); *A61M 2039/1077* (2013.01)

(58) Field of Classification Search
USPC .................................................. 604/164.01
See application file for complete search history.

(56) References Cited

U.S. PATENT DOCUMENTS

| | | | |
|---|---|---|---|
| 6,355,027 B1 * | 3/2002 | Le | A61M 25/0054 604/525 |
| 2002/0177814 A1 * | 11/2002 | Meng | A61M 25/0606 604/164.07 |
| 2009/0054845 A1 * | 2/2009 | Puhasmagi | A61L 29/06 604/180 |
| 2009/0157007 A1 | 6/2009 | McKinnon | |
| 2009/0192496 A1 * | 7/2009 | Suwito | A61M 25/0097 604/533 |

FOREIGN PATENT DOCUMENTS

| | | |
|---|---|---|
| DE | 29712676 U1 | 11/1997 |
| JP | S6068866 A | 4/1985 |
| JP | 2003507095 A | 2/2003 |
| JP | 2003339858 A | 12/2003 |
| JP | 2005512610 A | 5/2005 |
| JP | 2011506042 A | 3/2011 |
| JP | 2011510744 A | 4/2011 |
| WO | 94/01161 A1 | 1/1994 |
| WO | 2007005584 A1 | 1/2007 |
| WO | 2015133281 A1 | 9/2015 |

OTHER PUBLICATIONS

PCT International Search Report and Written Opinion in PCT/US2016/055666 dated Jan. 13, 2017, 13 pages.

* cited by examiner

CATHETER ADAPTER PROVIDING CATHETER KINK RESISTANCE

CROSS-REFERENCE TO RELATED APPLICATIONS

This application claims priority under 35 U.S.C. §119(e) to U.S. Provisional Application No. 62/247,256, filed Oct. 28, 2015, the disclosures of which are incorporated herein by reference in their entirety.

TECHNICAL FIELD

Aspects of the present disclosure relate to a vascular access device having a catheter and a catheter adapter including a flexible, kink resistant element to support the catheter as it transitions from the catheter adapter to a patient's vein and to prevent catheter kinking and occlusion.

BACKGROUND

Infusion therapy using catheters to administer fluids into and drain fluids out of the body has been a standard practice in medical procedures for years. Patients in a variety of settings including in hospitals, in home care, and other patients receive fluids, pharmaceuticals, and blood products via a vascular access device inserted into a patients vascular system. Catheters of various types and sizes have been used extensively by physicians in a variety of procedures including, but not limited to, treating an infection, providing anesthesia or analgesia, providing nutritional support, treating cancerous growths, maintaining blood pressure and heart rhythm, and many other clinically significant uses. However, catheter occlusion is a frequent complication experienced when using catheters in medical procedures and treatment. Catheter kinking results in a reduction of fluid volume delivery rate and, in many cases, causes a fluid stoppage and a rupture of the catheter wall with an accompanying loss of fluid.

Intravenous therapy is facilitated by vascular access devices located outside the vascular system of a patient (extravascular devices). Examples of extravascular devices that may access a patient's peripheral or central vasculature, either directly or indirectly include closed access devices, such as the BD Q-SYTE™ closed luer access device of Becton, Dickinson and Company; syringes; split septum devices; catheters; and intravenous (IV) fluid chambers. A vascular device may be indwelling for short term (days), moderate term (weeks), or long term (months to years). A vascular access device may be used for continuous infusion therapy or for intermittent therapy.

A common vascular access device is a plastic catheter that is inserted into a patient's vein. The catheter length may vary from less than one centimeter for peripheral access to many centimeters for central access. The catheter is commonly incorporated into a catheter adapter to aid in the ease of use, accessibility and utility of the catheter. A catheter adapter is generally a rigid, plastic, tubular member adapted to house one end of the catheter such that one end of the catheter is supported by the catheter adapter and the body and tip of the catheter extends beyond a first end of the catheter adapter. A catheter adapter generally further includes a second end adapted to receive additional infusion components for use with the catheter. For example, the second end of a catheter adapter may include a set of threads for attaching an intravenous line or for coupling a syringe to the catheter adapter to provide access to the patient's vasculature via the attached catheter.

The catheter may be inserted transcutaneously. When inserted transcutaneously, the insertion of the catheter is commonly aided by an introducer needle. The introducer needle is commonly housed inside the lumen of the catheter such that the gauge of the needle approximates the inner diameter of the catheter. The needle is positioned within the catheter such that the needle tip extends beyond the tip of the catheter such that the needle is used to penetrate the patient's vein and provide an opening for insertion of the catheter.

During insertion into a patient, the needle and catheter generally approach the patient's vein at an angle of about 30°, and the needle initially punctures the patient's epidermis and then continues into the vein. Once the needle and catheter tip enter the patient's vein, the needle and catheter are then repositioned so that the needle and catheter are brought into a position generally parallel with the patient's vein so that the needle and catheter may be inserted into the lumen of the patient's vein. When the catheter has been properly positioned within the patient's vein, the needle is removed from the lumen of the catheter and the catheter adapter is secured to the patient to prevent premature removal of the catheter. Typically the catheter adapter is secured to the patient by fastening the catheter adapter to the patient's skin via tape and/or other suitable securement device, and/or securement dressing. When securing the catheter adapter to the patient's skin, the root region of the catheter immediately exiting the catheter adapter must arch to accommodate the catheter's transition from the generally parallel, secured orientation of the catheter adapter, to the insertion angle of the catheter; an angle of approximately 30°.

General practice provides that the catheter be inserted into a patient such that an extended section of catheter is left between the patient and the catheter adapter to allow for transitional arching of the catheter. This exposed, archable length of catheter biases the catheter towards the patient's skin and thus the root region of the catheter experiences leverage forces because the catheter acts as a lever and the first end of the catheter adapter acts as a fulcrum exerting an upward force on the root region of the catheter. This upward force of the first end of the catheter adapter is undesirable due to the likelihood of occlusion of the root region of the catheter against the more rigid catheter adapter. Occlusion typically occurs as the patient and or the catheter is moved, increasing the angle of insertion in relation to the fixed position of the catheter adapter. For example, if the repositioning of the catheter and/or patient causes the catheter to be inserted further into the patient, the archable length of catheter between the patient and the catheter adapter decreases, which increases the angle of insertion and the upward force of the immobilized catheter adapter on the root region of the catheter. As the angle of insertion increases, the upward force of the catheter adapter also increases until the structural rigidity of the catheter wall is overcome, causing the catheter to kink.

Occlusion of the catheter is undesirable because occlusions slow or stop the flow through the catheter, creating undesirable backpressures that may cause the infusion system to malfunction and/or be damaged. Furthermore, occlusions reduce the efficiency of the infusion system, which could negatively affect treatment of the patient or the diagnostic procedure. Moreover, the exposed arched catheter section may become contaminated and pose a health risk to the patient. For example, an exposed section of catheter may become contaminated and then inserted into the patient as the patient and/or catheter is readjusted due to normal use by the patient and/or clinician. To reduce the likelihood of contamination and subsequent exposure to the patient, clinicians seek to minimize the length of exposed catheter by initially over-inserting the catheter into the patient. By reducing the length of exposed catheter, the upward force of the first end of the catheter adapter is increased, increasing the likelihood of occlusion within the root region of the catheter.

Contamination of the catheter and/or patient is undesirable for obvious reasons, the most obvious being that contamination may lead to secondary infection and/or complications unanticipated by the treating physician. Furthermore, a contaminated catheter may introduce a virus and/or bacteria to the patient that may conflict with the patient's primary therapy such that the patient is unable to receive further needed treatment.

Therefore, flexible, kink-resistant catheter adapters are desirable because they can reduce the possibility of occlusions and maintain a minimum fluid volume delivery rate. Although various attempts have been made to provide vascular access devices with a kink resistant catheter, there is still a need to provide a vascular access device that reduces the susceptibility of the catheter to kinking when flexed or bent during fluid delivery. It would also be desirable to provide a kink resistant catheter adapter that increases ease of penetration into a patient's vein, while providing the benefit of maintaining patency and flow rates throughout the life of the device. There is also a need for a vascular access device that allows for a steeper insertion angle which can be useful for subcutaneous injection as it supports the catheter as it is secured flat against the skin after a steep insertion.

SUMMARY

A first embodiment pertains to a vascular access device which comprises a catheter having a proximal end and a distal end, a catheter adapter having a distal end and a proximal end with an overall length extending from the distal end to the proximal end, an internal cavity, an upper portion, a lower portion, a tip region having a distal opening having a circumference through which the catheter extends, an introducer needle extending through the catheter, and a needle hub connected to the proximal end of the introducer needle. In one embodiment, the catheter adapter is connected to the proximal end of the catheter and at least a portion of the catheter adapter is made from a first material and at least a portion of the tip is made from a second material that is more flexible than the first material. In another embodiment, at least a majority portion of the catheter adapter is made from a first material and at least a portion of the tip is made from a second material that is more flexible than the first material. The portion of the tip made from the second material includes the tip having the distal opening having the circumference through which the catheter extends, wherein the catheter exiting the distal opening is flexibly supported by the tip. In one embodiment, the tip may include a flexible, kink resistant extension extending from the distal opening to provide support for the catheter.

In one embodiment, the vascular access device may further comprise a wing element attached to the catheter adapter and extending radially outward from the catheter adapter. In one embodiment, the wing element is made from the second material. In one embodiment, the vascular access device may further comprise at least one connecting channel formed between the wing element and the portion of the tip made from the second material. The connecting channel may be formed on an outside or inside surface of the catheter adapter. In one or more embodiments, the wing element and the portion of the tip are both made from the second material. In one or more embodiments, a wing element is molded directly on the catheter adapter.

In one or more embodiments, the first material and the second material have different durometer values. In one embodiment, the first material is a rigid polymeric material selected from one or more of a polyester, co-polyester, polycarbonate, polyethylene, polystyrene or polypropylene, and the second material is a flexible polymeric material. In one embodiment, the flexible polymeric material is selected from one or more of a thermoplastic elastomer, thermoplastic polyurethane, thermoplastic vulcanizate elastomer, olefin block copolymers, polyisoprene, or silicone. In one or more embodiments, the second material has a durometer value in the range of 30 Shore A to 90 Shore D, with a preferred range of −50 to 90 Shore A. Durometer hardness may be determined under test method ASTM D2240.

In one or more embodiments, the overall length of the catheter adapter is substantially equivalent at the upper portion and the lower portion, and the distal opening has an internal curvature defining a tapered region. In one embodiment, the internal curvature of the lower portion of the distal opening defines a chamfer.

The vascular access device may be a central venous catheter, a peripheral inserted central catheter, a peripheral intravenous cannula, an arterial catheter, or a mid-line catheter. In one or more embodiments, the catheter is made from polyurethane.

In one embodiment, the wing element comprises a first wing member extending from one side of the catheter adapter. In yet another embodiment, the wing element comprises a second wing member extending opposite the one side of the catheter adapter and the first wing. The second wing and the portion of the tip made from the second material are integrally molded.

In one embodiment, the vascular access device further comprises an extension tube extending from the catheter adapter and in fluid communication with the internal cavity of the adapter. In one or more embodiments, the vascular access device may also comprise a luer access, a blood control septum, an air vent and a notch in the introducer needle.

In one embodiment, the distal opening has an internal curvature defining a tapered region wherein the tapered region supports the catheter at the distal opening.

Another aspect of the disclosure pertains to a vascular access device comprising a catheter having a proximal end and a distal end, a catheter adapter having a distal end and a proximal end with an overall length extending from the distal end to the proximal end, an internal cavity, an upper portion, a lower portion and a tip having a distal opening having a circumference through which the catheter extends, an introducer needle having a distal end a proximal end, a needle hub connected to the proximal end of the introducer needle, and a flexible kink resistant extension extending from the distal opening of the tip to support the catheter adjacent the distal opening. The catheter adapter may be connected to the proximal end of the catheter.

In one embodiment, the catheter adapter is made from a first material and the flexible, kink resistant extension is made from a second material that is softer than the first material.

The extension may be either integral with the tip, or alternately, the extension and the tip may be separately molded.

In one or more embodiments, the vascular access device further comprises a wing element attached to the catheter adapter and extending radially outward from the catheter adapter. In one embodiment, the catheter adapter is made from a first material and the wing element and the flexible, kink resistant extension are made from a second material. In one embodiment, the first material is more rigid than the second material. The first material may be a rigid polymeric material selected from one or more of a polyester, co-polyester, polycarbonate, polyethylene, polystyrene or polypropylene. The second material is a flexible polymeric material selected from one or more of a thermoplastic elastomer (TPE), thermoplastic polyurethane (TPU), thermoplastic vulcanizate elastomer (TPV), olefin block copolymers (OBC), polyisoprene, or silicone.

In one embodiment, the wing element comprises a first wing member extending from one side the catheter adapter. In yet another embodiment, the vascular access device further comprises a second wing member extending opposite the one side of the catheter adapter.

In one embodiment, the distal opening has an internal curvature defining a tapered region wherein the tapered region supports the catheter at the distal opening.

DETAILED DESCRIPTION

Before describing several exemplary embodiments of the disclosure, it is to be understood that the description provided is not limited to the details of construction or process steps set forth in the following description. The devices described herein are capable of other embodiments and of being practiced or being carried out in various ways.

In this disclosure, a convention is followed wherein the distal end of the device is the end closest to a patient and the proximal end of the device is the end away from the patient and closest to a practitioner.

The disclosure describes various embodiments of a catheter adapter, which may be used in combination with other components such as a needle hub assembly including a needle to provide various vascular access devices. Vascular access devices according to one or more embodiments include but are not limited to central venous catheters, peripheral inserted central catheters, peripheral intravenous cannulas, arterial catheters, and mid-line catheters.

Referring to the drawings in which like reference characters refer to like parts throughout the several views thereof, FIGS. 1-7 illustrate a catheter adapter 18 and a vascular access device 10 in accordance with an embodiment of the present disclosure.

As shown in FIGS. 1-6, catheter adapter 18, which can be assembled with a hub assembly as described further below with respect to FIG. 7, includes a catheter 12 having a proximal end 14 and a distal end 16, a catheter adapter 18 having a distal end 20 and a proximal end 22, an overall length 24 extending from the distal end 20 to the proximal end 22, an internal cavity 26, an upper portion 28, a lower portion 30 and an adapter tip 32 having a catheter adapter tip opening 34 having a circumference through which the catheter 12 extends. As shown in FIGS. 1-4, the catheter adapter 18 is connected to the proximal end 14 of the catheter 12. An introducer needle 36 extends through the catheter 12. A needle hub 40 is connected to the proximal end 38 of the introducer needle 36. In one or more embodiment, at least a portion of the catheter adapter 18 is made from a first material and at least a portion of the adapter tip 32 is made from a second material that is more flexible than the first material. In a specific embodiment, at least a majority of the catheter adapter 18 is made from a first material and at least a portion of the adapter tip 32 is made from a second material that is more flexible than the first material. As used herein, "majority" means greater than 50% of the volume of catheter adapter. The catheter adapter 18 includes extends from the adapter tip 32 to the proximal end 22. In one or more embodiments, the first material and the second material have different durometer values. The first material is a rigid polymeric material selected from one or more of a polyester, co-polyester, polycarbonate, polyethylene, polystyrene or polypropylene, and the second material is a flexible polymeric material. In one or more embodiments, the flexible polymeric material is selected from one or more of a thermoplastic elastomer (TPE), thermoplastic polyurethane (TPU), thermoplastic vulcanizate elastomer (TPV), olefin block copolymers (OBC), polyisoprene, or silicone. In one or more embodiments, the second material has a durometer value in the range of 30 Shore A to 90 Shore D, with a preferred range of –50 to 90 Shore A. Durometer hardness may be determined under test method ASTM D2240.

As shown in FIGS. 1-6, the portion of the catheter adapter that is made from the second material is an extension 88, which protrudes distally from the catheter adapter tip 32. Thus in the embodiment shown, the portion of the catheter adapter 18 that is made from the second material include the extension 88 having a distal end 90 and a proximal end 92. In other embodiments, the catheter adapter 18 does not include extension 88, and the portion of the catheter adapter made from the second material includes distal tip region 94, which according to one or more embodiments includes only the distal tip region 94 that extends distally from the needle hub 40 to the catheter adapter tip 32. It will be understood that only a portion of the distal tip region 94 may be made from the second material. Thus, according to one or more embodiments, a majority of the catheter adapter 18 being made from first material means that 70-75%, or 75-80%, or 80-85%, or 85-99%, or 90-99%, or 90-98%, or 90-97%, or 90-96%, or 90-95% or 90-94% of the volume of the catheter adapter 18, excluding the wing element, is made from the first material, and the remainder of the volume of the catheter adapter is made from the second material. To determine the amount of the first material, the overall volume of the first material is determined, the overall volume of the second material excluding the wing element is determined, and the total volume of the catheter adapter is determined by adding the volume of the first material and the volume of the second material excluding the wing element. The percent of the first material is determined by dividing the volume of the first material divided by the total volume of the catheter adapter.

Catheter 12 is generally tubular and flexible comprising a shaft of uniform thickness having a length. Catheter 12 further includes a lumen 44. The diameter of the lumen 44 may vary and is selected to accommodate a desired flow rate and/or pressure from the intravenous (I.V.) fluid source.

Figure 6:
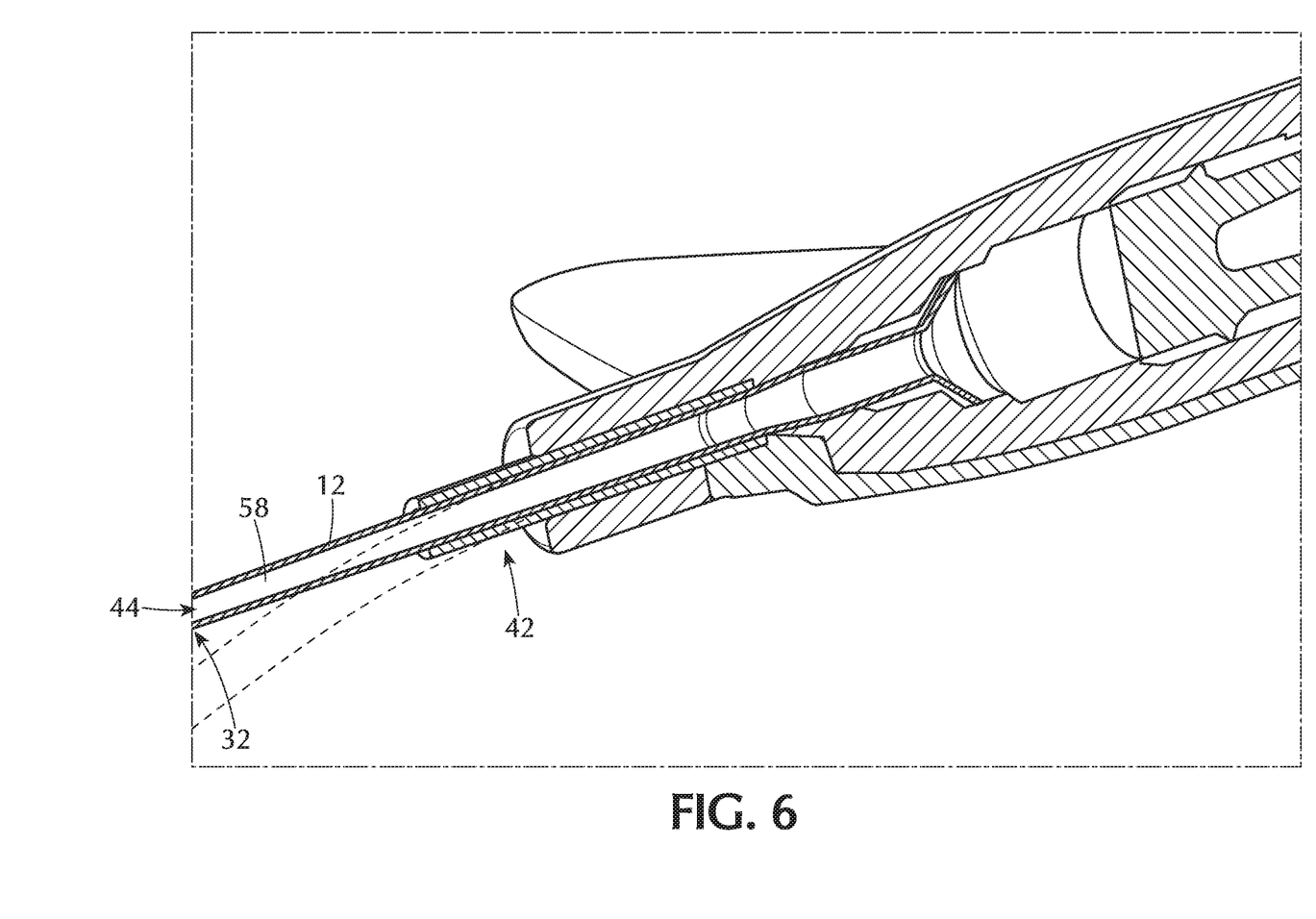
FIG. 6 is a cross-sectional view of the catheter adapter shown in FIG. 1 showing improved kink resistance provided by the device.

Catheter 12 further includes a flexured portion 42, which is shown in phantom in FIG. 6, as the catheter 12 is bent at the catheter adapter tip 32. Flexured portion 42 is defined as the uninserted section of the catheter between the first end of the catheter adapter tip opening and the catheter insertion site of the patient. The length is defined by the distance between flexured portion 42 of catheter 12 and catheter tip 31. The proximity of flexured portion 42 to the first end of the catheter adapter 18 makes the flexured portion prone to occlusion. This is because the first end of the catheter adapter exerts an upward force on flexured portion 42 when the catheter 12 is moved independent of and relative to the generally horizontal plane of the catheter adapter. The length of uninserted catheter, and therefore the point of maximum insertion, is selected such that a sufficient length of catheter remains uninserted. This allows the flexured portion of the catheter to gently bend in making the transition from the catheter adapter to the insertion site thereby preventing an occlusion due to over-insertion of the catheter.

In one or more embodiments, catheter 12 may be made from a biomaterial designed to reduce mechanical phlebitis and infiltration. In one or more embodiments, catheter 12 may be made from polyurethane. In a specific embodiment, the biomaterial may be a polyurethane that softens up to 70% in the vascular vein or artery to allow for increased patient comfort while providing kink resistance and improving catheter dwell time. Catheter 12 may be from 14 to 26 gauge.

Catheter 12 further includes a catheter tip 31. Catheter tip 31 includes a catheter opening 46 selected to provide clearance for introducer needle 36. Introducer needle 36 extends coaxially through a catheter of the catheter adapter. The diameter of the catheter opening 46 is selected to provide minimal tolerance between the outer surface of introducer needle 36 and the inner surface of catheter opening 46. As such, catheter tip 31 may provide a sufficiently sized access route into a patient's vein.

Figure 4:
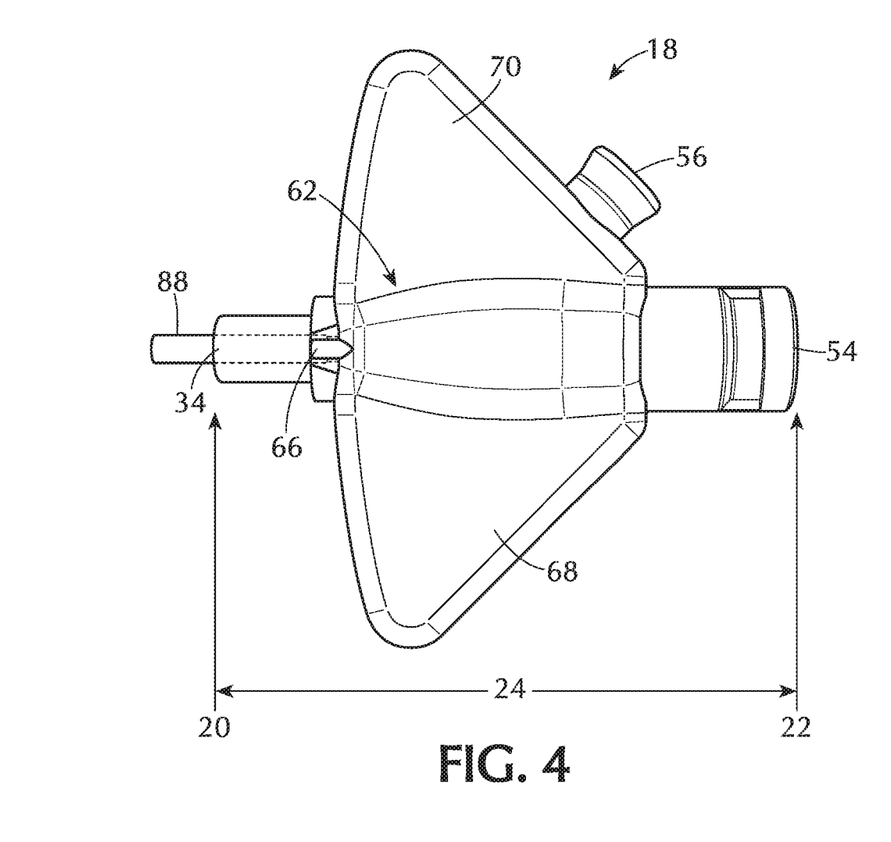
FIG. 4 is a bottom plan view of the catheter adapter shown in FIG. 1.

In one or more embodiments, a portion of adapter tip 32 made from the second material includes the tip having the distal opening having the circumference through which the catheter extends, and wherein a catheter exiting the distal opening is flexibly supported by the adapter tip 32. FIG. 4 shows the area of support of the integrally molded tip catheter transition kink resistant feature. The portion of adapter tip 32 made from the second material eliminates the non-supported, abrupt change in direction current catheters experience upon exiting the catheter adapter 18, thereby minimizing the localized stress on the catheter 12 and therefore minimizing the chance of collapsing and kinking the catheter and occluding the fluid flow.

In one or more embodiments, the first material and the second material have different durometer values. The first material may be a rigid polymeric material selected from one or more of a polyester, co-polyester, polycarbonate, polyethylene, polystyrene or polypropylene, and the second material is a flexible polymeric material. In one or more embodiments, the second material has a durometer value in the range of 30 Shore A to 90 Shore D, with a preferred range of −50 to 90 Shore A. Durometer hardness may be determined under test method ASTM D2240.

In one or more embodiments, the flexible polymeric material is selected from one or more of a thermoplastic elastomer (TPE), thermoplastic polyurethane (TPU), thermoplastic vulcanizate elastomer (TPV), olefin block copolymers (OBC), polyisoprene, or silicone.

In one or more embodiments, catheter adapter 18 is generally tubular and a majority of the catheter adapter is made from a rigid material, examples of which are provided above. The catheter 12 is incorporated into a catheter adapter 18 using industry standard methods. Catheter adapter 18 further includes a body 48 extending between the proximal end 22 and the distal end 20. The distal end 20 of the catheter adapter is generally tapered and includes and catheter adapter tip opening 34 through which the catheter 12 extends. The proximal end 22 generally includes an access port 54 for accessing lumen 44 of the catheter. Access port 54 may be a dual access port that provides multiple options for administration of fluid and medications.

Catheter adapter 18 may also be configured to house introducer needle 36 for inserting the catheter 12 into a patient. In one or more embodiments, introducer needle 36 includes a notch 58 to provide immediate confirmation of vessel entry at the point of insertion to improve first-stick success. An additional, optional feature of the catheter adapter 18 may include a lateral access port 56 extending from and being in fluid communication with the catheter adapter 18.

As shown in FIGS. 1-4 and 6-7, one or more embodiments of the catheter adapter 18 may include wing element 62. Wing element 62 is attached to the catheter adapter 18 and extends radially outward from the catheter adapter 18. In one or more embodiments wing element 62 is made from the second material.

In one or more embodiments, wing element 62 includes a first wing member 68 extending from one side of the catheter adapter 18. In yet another embodiment, the wing element includes a first wing member 68 extending in a first direction from the one side of the catheter adapter 18 and a second wing member 70 extending in a direction opposite to the first direction, and the first wing member 68, the second wing member 70 and the portion of the extension made from the second material are integrally molded. However, the first wing member and second wing member 70 need not be integrally molded, and each of these components can be separately molded from the same or different materials. In addition, while first wing member 68 and second wing member 70 are shown as being a contiguous piece to form the wing element 62, first wing member 68 and second wing member 70 can be separate pieces. In addition, according to one or more embodiments, the wing element can comprise a single wing member, either first wing member 68 or second wing member 70. Wing element 62 provides increased catheter stability and therefore increase dwell time. In one or more embodiments, the first wing member 68 and the second wing member 70 may be made from the second material to create a soft and flexible wing to ensure patient comfort.

Figure 1:
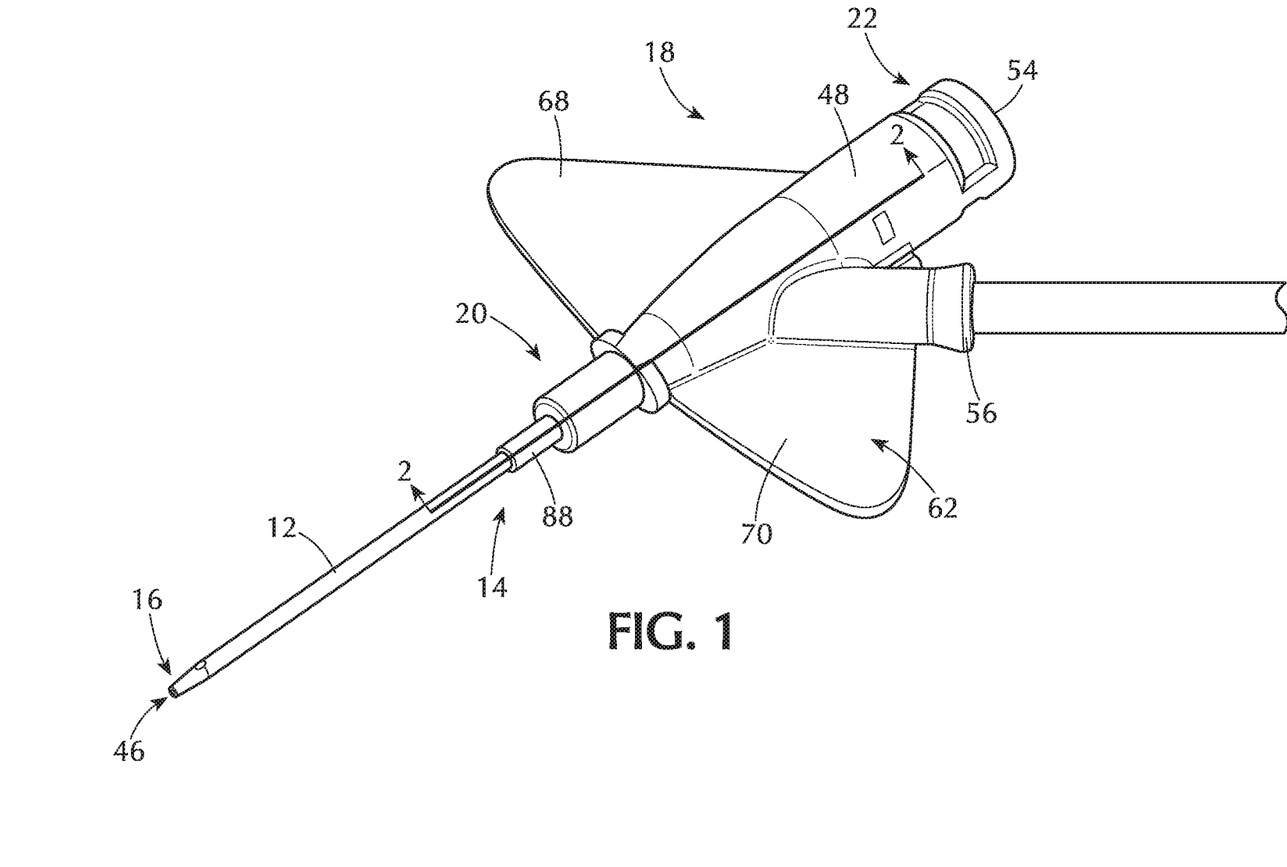
FIG. 1 illustrates a perspective view of a catheter adapter according to a first embodiment.
Figure 2:
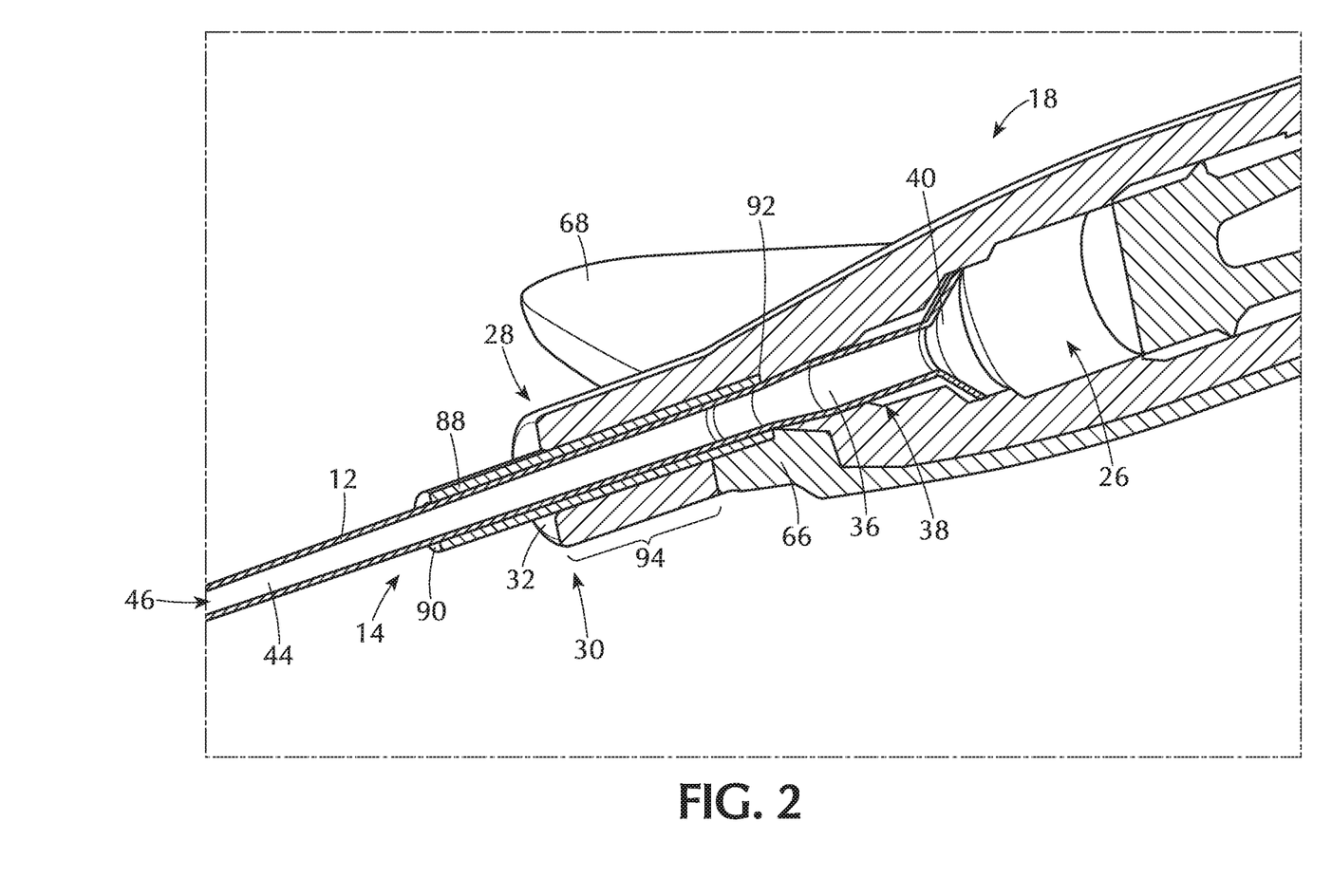
FIG. 2 is a sectional view of the catheter adapter shown in FIG. 1 taken along lines 2-2.
Figure 3:
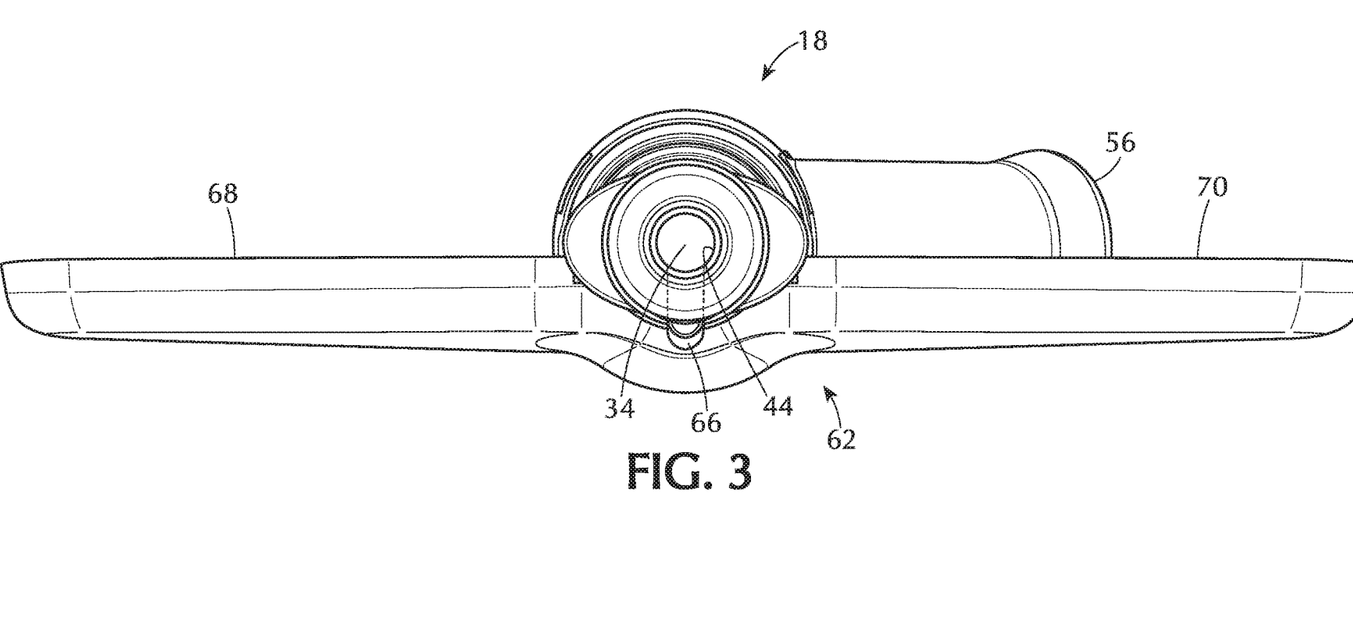
FIG. 3 is a distal end view of the catheter adapter shown in FIG. 1.

In yet another embodiment, at least one connecting channel is formed on an inside surface of the catheter adapter to provide an internal connecting channel 66. As shown in FIG. 2, the internal connecting channel 66 is formed between the adapter tip 32 and the wing element 62. Internal connecting channel 66 minimizes any potential impact to the nose external geometry of the catheter adapter. Internal connecting channel 66 may be made using a two shot manufacturing process to integrally mold the flexible tip at the catheter transition point with wing element 62. A first shot is the first material which makes up a majority of the catheter adapter 18 and a second shot is the second material which makes up a portion of the adapter tip 32.

In use, the catheter adapter 18 is secured to a patient and the catheter tip 31 is inserted into the patient's vascular system. The catheter 12 is positioned and inserted within the patient's vascular system at a determined insertion angle. The insertion angle may include any angle necessary to introduce the catheter into the patient's vascular system. For example, an insertion angle may be selected within the range of 1° to 90°, with a preferable range of angle of insertion from 5° to 45°.

Following insertion of the catheter, the flexured portion of the catheter is bent in a general arch shape to accommodate the transition of the catheter from the catheter adapter to the catheter insertion site. This feature also allows for a steeper insertion angle which can be useful for subcutaneous injection as it supports the catheter as it is secured flat against the skin after a steep insertion.

Upon insertion of the catheter into the insertion site, the catheter experiences higher leverage forces. Thus, the catheter acts as a lever and the rigid first end of the catheter adapter acts as a fulcrum exerting an upward force on the catheter. As the catheter is inserted further into the insertion site, the upward force of the catheter is dissipated by the portion of the flexible tip of the catheter adapter made from the second material wherein the tip also bends with the catheter to prevent kinking and occlusion of the catheter. Therefore, according to one or more embodiments of the present disclosure, wherein the vascular access device has a majority of the catheter adapter 18 made from a first material and at least a portion of the adapter tip 32 is made from a second material that is more flexible than the first material the flexible tip of the catheter adapter made from the second material, patency and flow rates are maintained throughout the life of the device. This is particularly useful in cases of drawing blood from an indwelling peripheral intravenous catheter, peripheral inserted central catheter or central venous catheter vascular access device.

Figure 5:
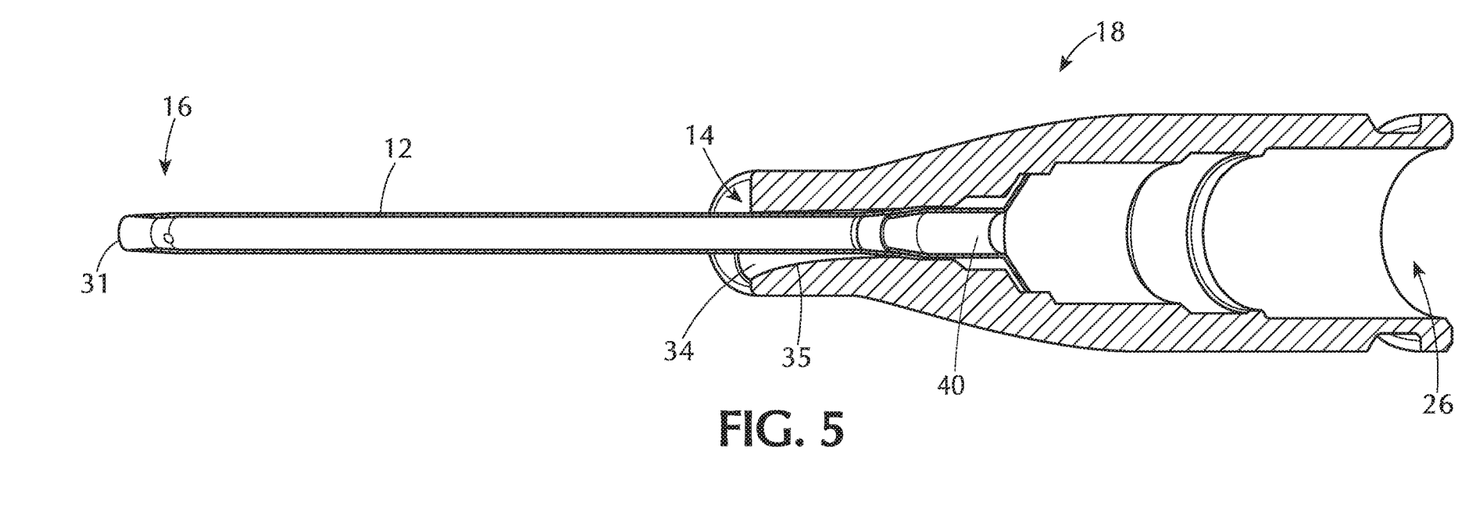
FIG. 5 is a cross-sectional view of a catheter adapter including a chamfered opening.

In one or more embodiments, and as shown in FIG. 5, the catheter adapter tip opening 34 is rounded, curved or chamfered at surface 35 such that the opening includes an arch of no more than 90°. The degree of curvature is selected to support the flexured portion of the catheter in maintaining an insertion angle within the desired range. In this embodiment, the flexured portion of the catheter is bent over and along the contour of the rounded or curved over catheter adapter tip opening 34. The flexured portion is supported by the rounded opening in maintaining the necessary degree of curve for the catheter so as to avoid an occlusion and maintain the optimal degree of insertion. The rounded opening minimizes the fulcrum function of the distal end of the catheter adapter on the flexured portion of the catheter such that the catheter may be maximally inserted into the patient with minimal upward force of the distal end of the catheter. This minimizes the likelihood of occlusion.

In one or more embodiments, the distal opening has an internal curvature defining a tapered region at surface 35 wherein the tapered region supports the catheter at the distal opening. After insertion of the catheter, the tapered region provides transitional support at an angle of insertion for the catheter without restricting flow through the catheter.

As shown in FIG. 5, the overall length of the catheter adapter is substantially equivalent at the upper portion and the lower portion, and the distal opening has an internal curvature defining a tapered region, and wherein the internal curvature of the lower portion of the distal opening defines a chamfer.

In one or more embodiments, the catheter adapter tip opening 34 is chamfered such that the tolerance between the distal end of the catheter adapter and the flexured portion of the catheter is increased. Thus, the flexured portion of the catheter may bend more sharply before the catheter contacts the catheter adapter tip opening resulting in an occlusion. In one embodiment, the catheter adapter tip opening is chamfered at an angle which is less than 90° relative to the generally horizontal plane. The chamfered opening permits a greater length of catheter to be inserted before an occlusion occurs due to the delayed contact of the tip opening and the catheter. Therefore, as the flexured portion of the catheter is further inserted into the patient, the flexured portion is allowed to bend to a greater degree before contacting and pivoting on the tip opening resulting in an occlusion of the catheter at the flexured portion.

In one or more embodiments, the catheter adapter 18 is made from a first material and the flexible, kink resistant extension 88 is made from a second material that is softer than the first material. In another embodiment, kink resistant extension 88 may be made from the same material as catheter adapter 18, however, kink resistant extension 88 may be made of a thinner section of material to enable kink resistant extension 88 to be more flexible than catheter adapter 18. In one or more embodiments, kink resistant extension 88 may be integral with the adapter tip 32 or the extension 88 and the adapter tip 32 may be separately molded.

Figure 8:
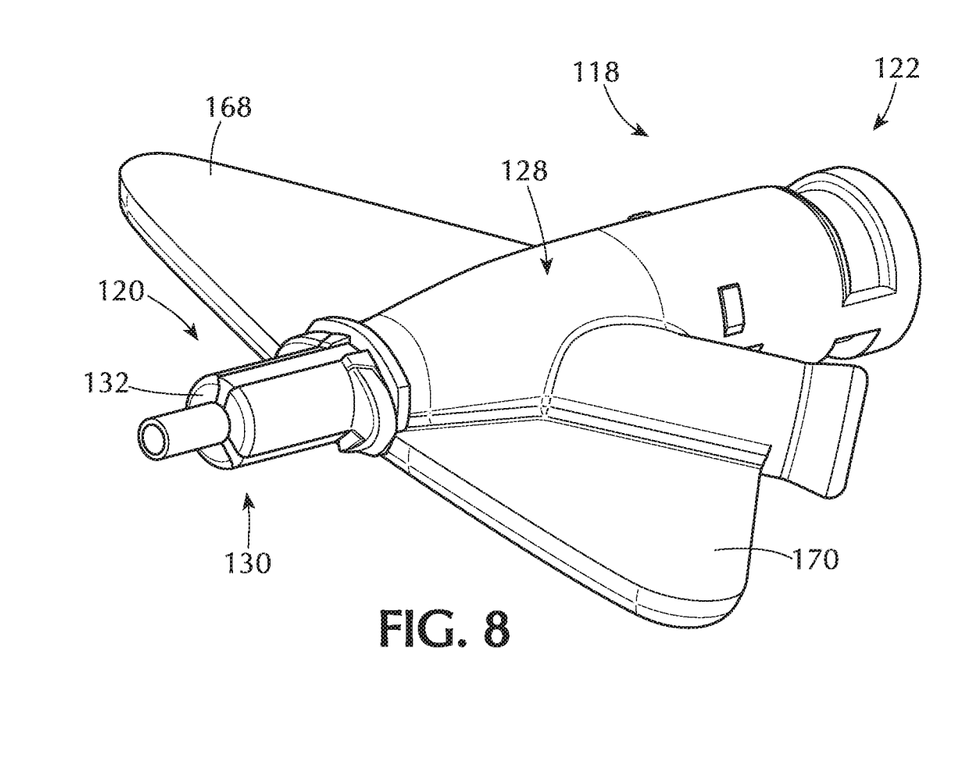
FIG. 8 is a top perspective view of a catheter adapter according to a second embodiment.
Figure 9:
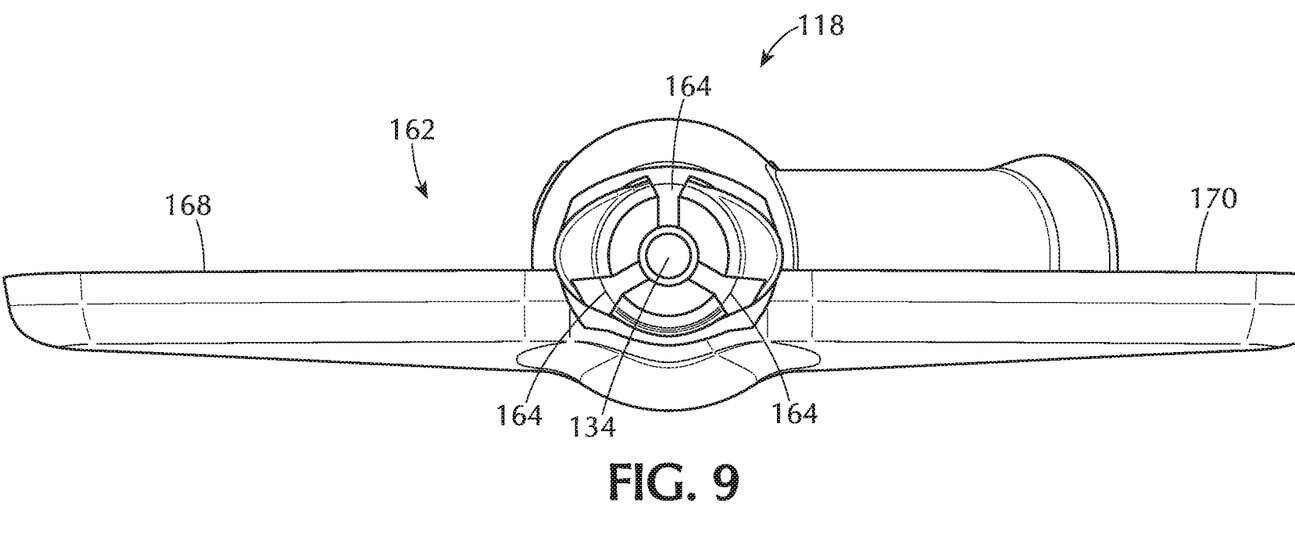
FIG. 9 is a distal end view of the catheter adapter in FIG. 8.
Figure 10:
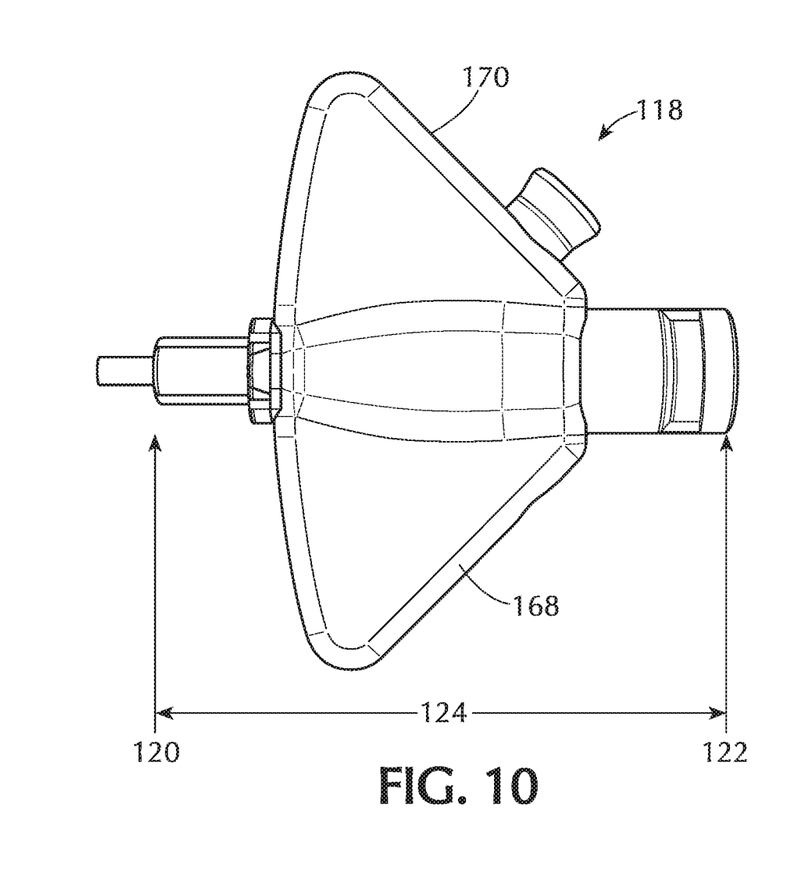
FIG. 10 is a bottom plan view of the catheter adapter in FIG. 8.

FIGS. 8-10 show an embodiment in which the catheter adapter 118 is substantially the same as the catheter adapter 118 described with respect to FIGS. 1-4 and 6, except for the connecting channel as described further below. The catheter adapter 118 has a distal end 120 and a proximal end 122, an overall length 124 extending from the distal end 120 to the proximal end 122, an upper portion 128, a lower portion 130 and an adapter tip 132 having a distal opening 134 having a circumference through which the catheter (not shown) extends. A majority of the catheter adapter, as described above, is made from a first material and at least a portion of the adapter tip 132 is made from a second material that is more flexible than the first material. As used herein, "majority" means greater than 50% of the volume of catheter adapter, and includes the ranges provided above. A portion of the adapter tip 132 includes at least one external connecting channel 164 formed on an outside surface of the catheter adapter and continuously extending between the adapter tip 132 and optional wing element 162. In one or more embodiments, the wing element 162 and the portion of the adapter tip are both made from a second material. In one or more embodiments, wing element 162 is molded directly on the catheter adapter.

Optional wing element 162 is attached to the catheter adapter 18 and extends radially outward from the catheter adapter 118. In one or more embodiments, wing element 162 is made from the second material.

In one or more embodiments, wing element 162 includes a first wing member 168 extending from one side of the catheter adapter 118. In yet another embodiment, the wing element includes a first wing member 168 extending in a first direction from the one side of the catheter adapter 118 and a second wing member 170 extending in a direction opposite to the first direction, and the first wing member 168, the second wing member 170 and the portion of the extension made from the second material are integrally molded. However, the first wing member and second wing member 170 need not be integrally molded, and each of these components can be separately molded from the same or different materials. In addition, while first wing member 168 and second wing member 170 are shown as being a contiguous piece to form the wing element 162, first wing member 168 and second wing member 170 can be separate pieces. In addition, according to one or more embodiments, the wing element can comprise a single wing member, either first wing member 168 or second wing member 170. Wing element 162 provides increased catheter stability and therefore increase dwell time. In one or more embodiments, the first wing member 168 and the second wing member 170 may be made from the second material to create a soft and flexible wing to ensure patient comfort.

In one or more embodiments, the first material and the second material have different durometer values. The first material may be a rigid polymeric material selected from one or more of a polyester, co-polyester, polycarbonate, polyethylene, polystyrene or polypropylene, and the second material is a flexible polymeric material. In one or more embodiments, the flexible polymeric material is selected from one or more of a thermoplastic elastomer (TPE), thermoplastic polyurethane (TPU), thermoplastic vulcanizate elastomer (TPV), olefin block copolymers (OBC), polyisoprene, or silicone. In one or more embodiments, the second material has a durometer value in the range of 30 Shore A to 90 Shore D, with a preferred range of −50 to 90 Shore A. Durometer hardness may be determined under test method ASTM D2240.

The at least one external connecting channel 164 is formed on an outside surface of the catheter adapter between the wing element 162 and the portion of the adapter tip 132 made from the second material. The catheter adapter 118 can be formed using a two shot injection molding process in which a first material making up a majority of the catheter adapter 118 is injected into the mold and a second material making up at least a portion of the adapter tip 132 is injected into the mold.

Figure 7:
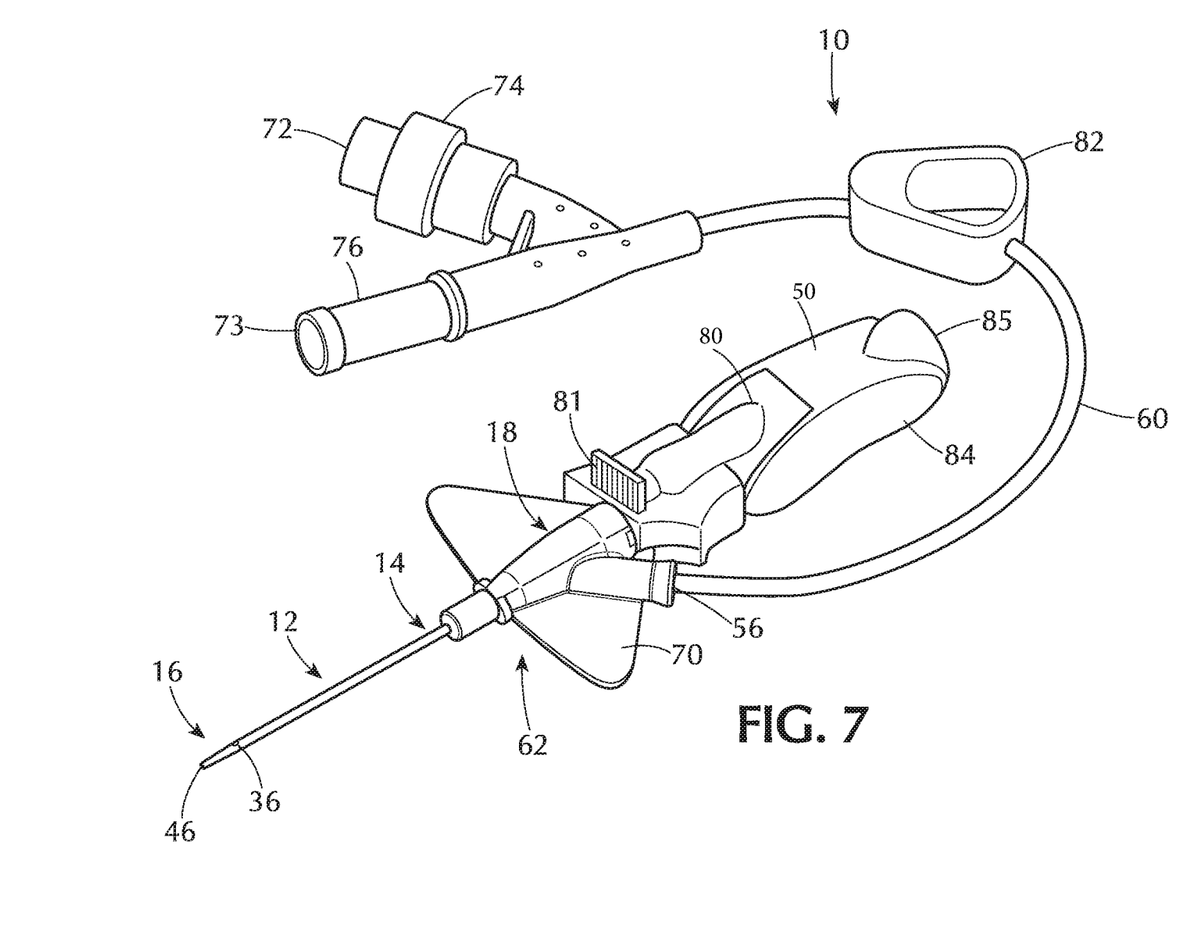
FIG. 7 illustrates a perspective view of one or more embodiments of a vascular access device including a catheter adapter.

The catheter adapter 118 described with respect to FIGS. 8-10 can be used as part of a vascular access device described with respect to FIG. 7. Thus, as described further below, the catheter adapter 18 described with respect to FIG. 7 may be substituted with the catheter adapter 118 described with respect to FIGS. 8-10.

As shown in FIG. 7, the catheter adapter 18 may be part of a vascular access device 10, with additional components in fluid communication with the catheter adapter 18. As shown in FIG. 7, the lateral access port 56 may be connected to a section of extension tube 60 for establishing fluid communication between an IV fluid source and the internal cavity 26 of the catheter adapter or lumen 44 of the catheter. In one or more embodiments, the extension tube 60 extends in line with or laterally with the body of the catheter adapter. In one or more embodiments, the extension tube 60 is built-in to reduce contamination and mechanical phlebitis by eliminating manipulation at the insertion site. In one or more embodiments, the extension tube 60 is compatible with high pressure injection. In one or more embodiments, the extension tube 60 provides continuous confirmation of vessel access during advancement of the catheter into the patient vein.

In one or more embodiments, the needle hub assembly 50 is assembled with the catheter adapter by inserting the needle into the lumen 44 of the catheter 12. The needle hub assembly is shown as including finger grips 84 positioned at the sides of the needle hub assembly 50 to facilitate various insertion techniques. In one or more embodiments, bumps may be present on the finger grip to indicate where to the user may grip the device for needle removal. In one or more embodiments, a thumb pad 85, having a gently convex surface, is provided at the proximal end of the needle hub assembly 50. A flange 86, having a gently convex surface, is provided at the proximal end of the hub assembly to provide a finger pad.

First wing members 68, second wing member 70, thumb pad 85 and flange 86 may be utilized by the user during insertion, permitting the user to elect which insertion technique to employ.

In one or more embodiments, the needle hub assembly 50 includes a needle shield 80. The needle shield may be a design adapted to secure the tip of the needle within the shield after use. In one or more embodiments, the needle shield may be activated passively to ensure compliance with compromising user technique. The needle tip is completely covered by the needle shield in a fixed position. In one or more embodiments, a ferrule, crimp or other structure may be included near the tip for engagement with a needle shield in certain applications.

A push tab 81 may be provided to facilitate catheter advancement during insertion. The push tab also allows for one-handed or two-handed advancement. In one or more embodiments, the push tab is removed with the needle shield. A clamp 82 may also be included on the extension tubing to prevent blood flow when replacing the access port.

The proximal end of the introducer needle may be crimped to provide a fluid-tight seal around the proximal end of the introducer needle. The introducer needle may be glued or mechanical interlocks may be formed to secure the introducer needle to the hub.

In one or more embodiments, the vascular access device 10 further includes a first luer access 72 and a second luer access 73 in fluid communication with the extension tube 60, a blood control split septum 74 associated with the first luer access 72, and an air vent 76 associated with the second luer access 73. Split septum 74 allows for a reduction in catheter-related bloodstream infection (CRBSI) while providing unrestricted flow and a straight fluid path and functions as a blood control septum. In one or more embodiments, the split septum 74 may be located in an internal cavity of the catheter adapter or on the distal end of the catheter adapter. In yet another embodiment, the split septum 74 may be located on a distal end of the extension tube 60. The air vent 76 allows air to escape from the system during insertion, providing continuous confirmation of vascular access while preventing leakage of blood from the system during insertion. In one or more embodiments, the air vent 76 may be at the distal end of extension tube 60.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments,"

"in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A vascular access device comprising:
   a catheter having a proximal end and a distal end;
   a catheter adapter having a distal end, a proximal end, an overall length extending from the distal end to the proximal end, an internal cavity, an upper portion, a lower portion and a tip region having a distal opening having a circumference through which the catheter extends, the catheter adapter being connected to the proximal end of the catheter;
   an introducer needle extending through the catheter;
   a wing element;
   an internal connecting channel formed on an inside surface of the catheter adapter, the internal connecting channel being formed between the wing element and the adapter tip of the catheter adapter, the internal connecting channel configured to minimize impact to the tip; and
   a needle hub connected to the proximal end of the introducer needle;
   wherein at least a portion of the catheter adapter is made from a first material and at least a portion of the tip and the wing element is made from a second material that is more flexible than the first material;
   wherein the tip includes a flexure portion, and the distal opening of the tip being chamfered at an angle which is less than 90° relative to a generally horizontal plane of the catheter adapter.

2. The vascular access device of claim 1, wherein the portion of the tip made from the second material includes the tip having the distal opening having the circumference through which the catheter extends, and wherein a catheter exiting the distal opening is flexibly supported by the tip.

3. The vascular access device of claim 2, wherein the wing element is attached to the catheter adapter and extending radially outward from the catheter adapter.

4. The vascular access device of claim 1, wherein the first material and the second material have different durometer values.

5. The vascular access device of claim 4, wherein the first material is a rigid polymeric material selected from one or more of a polyester, co-polyester, polycarbonate, polyethylene, polystyrene or polypropylene, and the second material is a flexible polymeric material.

6. The vascular access device of claim 5, wherein the flexible polymeric material is selected from one or more of a thermoplastic elastomer, thermoplastic polyurethane, thermoplastic vulcanizate elastomer, olefin block copolymers, polyisoprene, or silicone.

7. The vascular access device of claim 1, wherein the at least one connecting channel is formed on an outside surface of the catheter adapter.

8. The vascular access device of claim 1, wherein the at least one connecting channel is formed on an inside surface of the catheter adapter.

9. The vascular access device of claim 1, wherein the overall length of the catheter adapter is substantially equivalent at the upper portion and the lower portion, and the distal opening has an internal curvature defining a tapered region, and wherein the internal curvature of the lower portion of the distal opening defines a chamfer.

10. The vascular access device of claim 1, wherein the vascular access device is selected from the group consisting of a central venous catheter, a peripheral inserted central catheter, a peripheral intravenous cannula, an arterial catheter, and a mid-line catheter.

11. The vascular access device of claim 3, wherein the wing element comprises a first wing member extending from one side of the catheter adapter.

12. The vascular access device of claim 11, wherein the wing element comprises a second wing member extending opposite the one side of the catheter adapter, and the first wing, the second wing and the portion of the tip made from the second material are integrally molded.

13. The vascular access device of claim 1, further comprising an extension tube extending from the catheter adapter and in fluid communication with the internal cavity of the adapter.

14. The vascular access device of claim 13, further comprising at least one of a luer access, a blood control septum, an air vent and a notch in the introducer needle.

15. The vascular access device of claim 1, wherein the tip includes a flexible, kink resistant extension extending from the distal opening to provide support for the catheter.

16. The vascular access device of claim 1, wherein the catheter is made from polyurethane.

17. The vascular access device of claim 1, wherein the distal opening has an internal curvature defining a tapered region wherein the tapered region supports the catheter at the distal opening.

18. The vascular access device of claim 1, wherein at least a majority portion of the catheter adapter is made from a first material and at least a portion of the tip is made from a second material that is more flexible than the first material.

19. A vascular access device comprising:
   a catheter having a proximal end and a distal end;
   a catheter adapter having a distal end, a proximal end, an overall length extending from the distal end to the proximal end, an internal cavity, an upper portion, a lower portion and a tip having a distal opening having a circumference through which the catheter extends, the catheter adapter being connected to the proximal end of the catheter, the catheter adapter is made from a first material;
   an introducer needle having a distal end and a proximal end;
   a needle hub connected to the proximal end of the introducer needle; and
   a flexible, kink resistant extension protruding distally from the distal opening of the catheter adapter tip to support the catheter exiting from the distal opening of the catheter adapter tip, the kink resistant extension is made from a second material that is softer than the first material; and,
   an internal connecting channel formed on an inside surface of the catheter adapter, the internal connecting channel being formed between the wing element and the adapter tip of the catheter adapter, the internal connecting channel configured to minimize impact to the tip wherein the distal opening has an internal curvature defining a tapered region wherein the tapered region supports the catheter at the distal opening.

20. The vascular access device of claim 19, wherein the extension is integral with the tip.

21. The vascular access device of claim 19, wherein the extension and the tip are separately molded.

22. The vascular access device of claim 19, further comprising a wing element attached to the catheter adapter and extending radially outward from the catheter adapter, wherein the catheter adapter is made from a first material and the wing element and the flexible, kink resistant extension are made from a second material, wherein the first material is more rigid than the second material.

23. The vascular access device of claim 19, wherein the first material is a rigid polymeric material selected from one or more of a polyester, co-polyester, polycarbonate, polyethylene, polystyrene or polypropylene, and the second material is a flexible polymeric material.

24. The vascular access device of claim 23, wherein the flexible polymeric material is selected from one or more of a thermoplastic elastomer (TPE), thermoplastic polyurethane (TPU), thermoplastic vulcanizate elastomer (TPV), olefin block copolymers (OBC), polyisoprene, or silicone.

25. The vascular access device of claim 19, wherein the vascular access device is selected from the group consisting of a central venous catheter, a peripheral inserted central catheter, a peripheral intravenous cannula, an arterial catheter, and a mid-line catheter.

26. The vascular access device of claim 22, wherein the wing element comprises a first wing member extending from one side the catheter adapter.

27. The vascular access device of claim 26, further comprising a second wing member extending opposite the one side of the catheter adapter.

28. The vascular access device of claim 19, wherein the catheter is made from polyurethane.

* * * * *